United States Patent [19]

Goodwin et al.

[11] Patent Number: 4,528,162
[45] Date of Patent: Jul. 9, 1985

[54] DISTILLATION APPARATUS

[75] Inventors: Anton E. Goodwin; Janet L. Marton; Robert M. Owens; Jackie W. Whisenhunt; Roy D. Swain, all of Ponca City, Okla.

[73] Assignee: Conoco Inc., Ponca City, Okla.

[21] Appl. No.: 409,191

[22] Filed: Aug. 18, 1982

[51] Int. Cl.³ .......................... B01D 3/06; G01N 1/00
[52] U.S. Cl. .................................. 422/101; 202/197; 203/88; 203/DIG. 2
[58] Field of Search .................. 422/101; 203/DIG. 2, 203/40, 88; 202/197

[56] References Cited

U.S. PATENT DOCUMENTS

| 1,931,895 | 10/1933 | Grote et al. | 422/101 X |
| 2,816,064 | 12/1957 | Smith | 203/40 X |
| 3,271,111 | 9/1966 | Boyd, Jr. et al. | 436/124 |
| 3,992,151 | 11/1976 | Vanderhoeden | 436/124 X |

FOREIGN PATENT DOCUMENTS 1051804 12/1981 Japan ................................. 422/101

Primary Examiner—Arnold Turk
Attorney, Agent, or Firm—Cortlan R. Schupbach

[57] ABSTRACT

An improved distillation apparatus is disclosed containing expansion means and vapor draw means surrounded by heating means to provide vapor/liquid phase separation entirely within the heating bath. The apparatus is especially useful for determining phenol content in refinery waste streams.

4 Claims, 2 Drawing Figures

DISTILLATION APPARATUS

This invention relates to distillation apparatus having an expansion chamber and vapor draw means included within heating means in order to control the vapor/liquid interface and to avoid altering the vapor/liquid interface within the distillation apparatus as temperature and flow rate change.

Distillation apparatus have been known to the art for years. Representative but non-exhaustive examples of such apparatus as those disclosed in U.S. Pat. Nos. 3,354,052; 3,051,895 and 3,505,173. Representative but non-exhaustive examples of references showing the use of such apparatus with sampling and analyzing devices are U.S. Pat. Nos. 3,807,233; 3,985,624; 4,080,171 and 4,250,142. However, these apparatus all have a common failing upon continuous distillation when flow rates and/or temperature are changed, in that separation of the vapor-liquid interface tends to move erratically outside the apparatus, thereby failing to adequately separate the components undergoing distillation. It would therefore be of great benefit to provide an improved distillation apparatus which would be relatively insensitive to changes in distilland flow and temperature and which would allow substantially complete separation of the distilland components.

It is therefore an object of the present invention to provide a distillation apparatus to decrease sensitivity to distilland flow rate and temperature. Other objects will become apparent to those skilled in this art as the description proceeds.

We have now invented a distillation apparatus comprising (1) a casing means containing therein closed conduit for liquid distilland, said conduit surrounded by heating means, contained within said casing means; (2) a vapor draw means connected directly to said closed distilland conduit, said vapor draw means containing at least one expansion chamber substantially vertically disposed in and surrounded by said heating means, the lower portion of the lowest of said expansion chambers containing inert particulate means to increase surface area; (3) a bottoms draw means disposed in said heating means and connected to the lower portion of the lowest expansion chamber of a vapor draw means, said bottom draw means exiting substantially vertically from said lowest chamber and being substantially totally filled with said inert particulate means. The apparatus described is particularly useful in continuous flow analysis. The apparatus has been useful for phenol determination of refinery affluents.

Determination of phenol in refinery effluents undergoing continuous distillation has been previously carried out. However, changing the feedrate of distilland to the distillation unit and changing the temperature of the heating bath caused changes in the determined phenol concentration from the distilland. We have found, for example, that apparent phenol concentration for the same sample of a typical refinery effluent varies from about 200 parts per billion to about 2000 parts per billion as the rate of feed changed from 1.6 to 3.9 milliliters per minute (mls/min) and temperature was changed from 130° C. to 200° C.

We discovered that the addition of an expansion chamber at the end of a conventional distillation coil places the interface between liquid and vapor phases in the heating area for better temperature control. An expansion chamber located in the heating bath, together with the addition of a layer of inert particular material (such as glass beads) at the bottom of the expansion chamber increases the area of the interface and provides for better exchange of heat. In a simple distillation (a distillation without reflux) it is important to have such a large surface area for the interface to provide good heat transfer. In addition, a draw of liquid phase from the bottom of the expansion chamber is important in a continuous simple distillation process in order to effect good separation of volatiles from the liquid phase.

We have discovered that the new design substantially eliminates feed rate of distilland to the distillation unit as a parameter affecting phenol concentration in the distillant analyzed. In addition, at heating bath temperatures greater than 200° C., the phenol concentration flattened to a maximum value, thereafter giving a temperature range where phenol concentrations no longer vary.

DETAILED DESCRIPTION OF THE DRAWINGS

Figure 1:
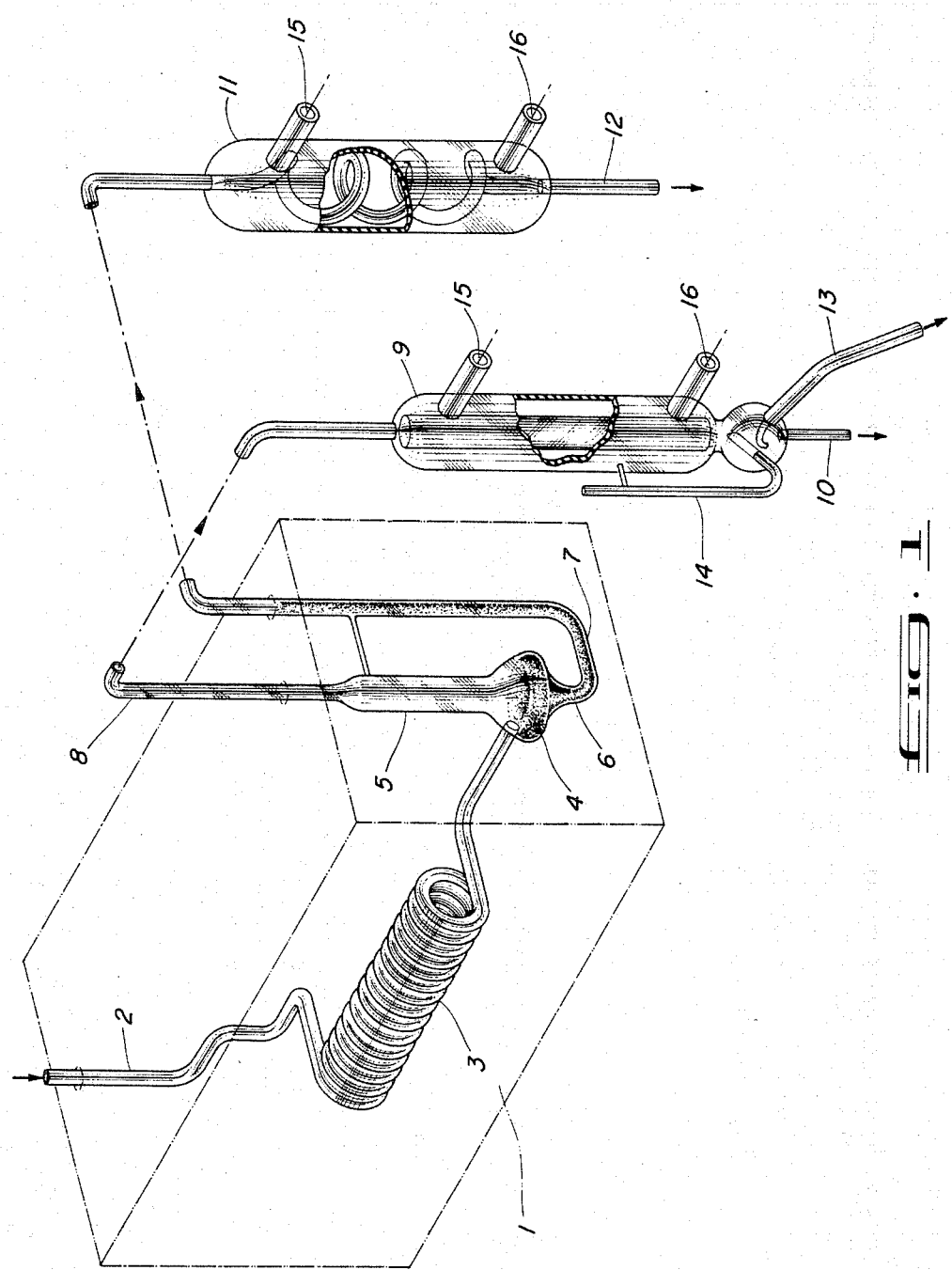
FIG. 1 shows the modified distillation apparatus of the present invention in a preferred embodiment.

FIG. 1 shows the modified distillation apparatus of the present invention in a preferred embodiment. The apparatus is contained within a heating bath (1) and distilland enters the apparatus through line (2). The distilland then passes through a series of coils (3) to extend residence time in the heating bath (1). The distilland exits the coils into an expansion chamber area (4) which contains at least one expansion chamber, optionally enlarged (5). The vapor/liquid interface is separated in expansion chambers (4) and (5), bottoms product exiting the expansion chamber through line (6) filled with inert particulate means (7). The overhead distillate exits the heating bath expansion chamber through line (8), passes through a condenser (9) and exits the condenser through line (10) for sampling. A liquid draw is placed on the bottom through line (6) then passes to a heat exchanger (11). The bottoms exit the heat exchanger through line (12) and are disposed. The figure also shows entrance (16) and exit (15) for cooling fluid to condenser jackets.

Figure 2:
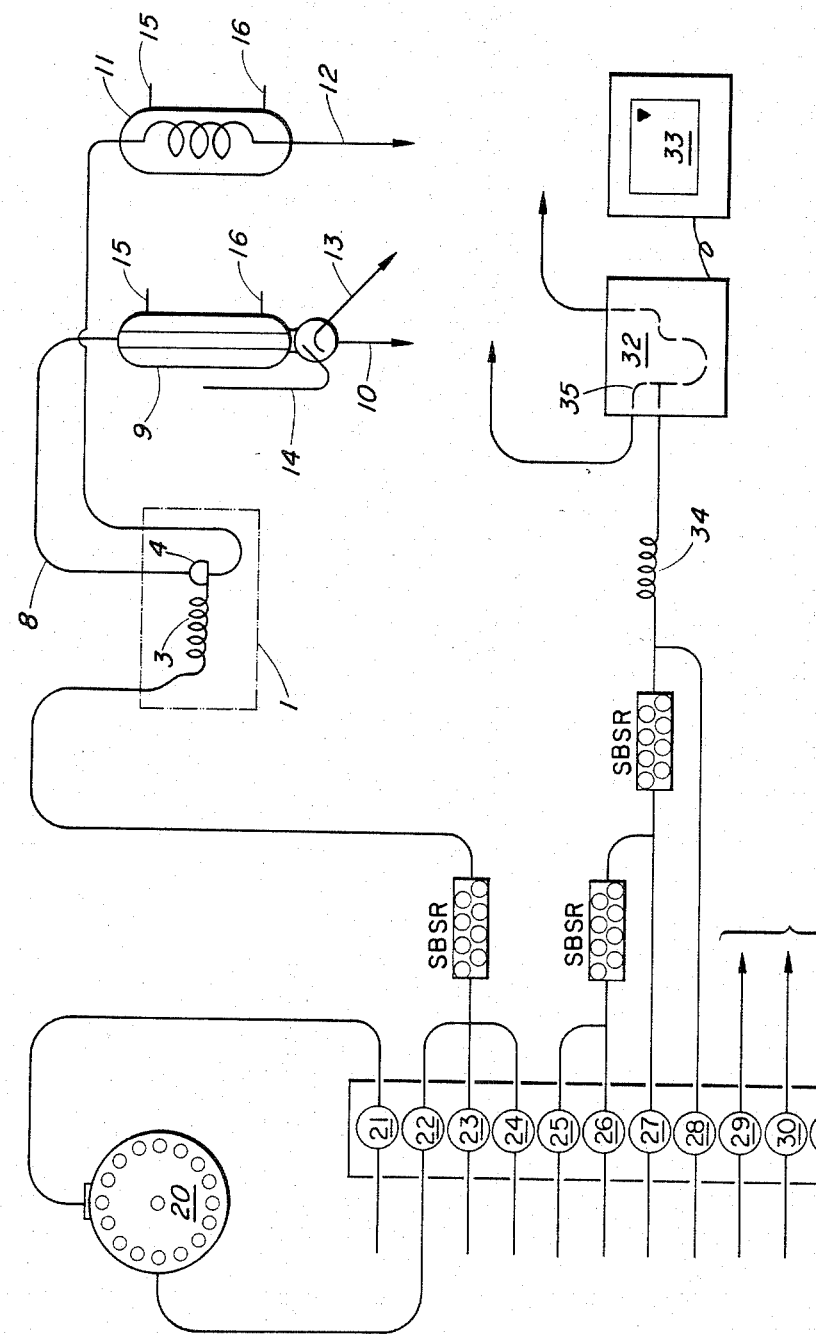
FIG. 2 describes a flow manifold for the colormetric determination of phenol which is useful in continuous analysis.

FIG. 2 is a detailed description of a full manifold for phenol determination utilizing continuous analysis of refinery samples. This apparatus has been very useful for continuous monitoring of refinery streams. In the figure, samples are automatically drawn from the sampler (20) and are placed into a sample manifold. In the sample manifold, (21) denotes washwater while (22) is the sample from the sampler; (23) denotes $H_3PO_4$, (24) denotes air. (25) denotes a resample stream from 10 and (26) denotes 4-aminoantipyrine, in buffer solution, (27) denotes potassium ferricyanide in buffer solution, (28) denotes air, (29) denotes level control from 13, (30) denotes acid bottoms from 12 and (31) denotes a debubbler pull. The legend SBSR denotes a single bead string reactor, which provides excellent mixing of the components on the way to distillation and/or analysis and (34) is a glass mixing coil.

In practice, the system is washed with washwater, whereupon the manifold shifts in order to combine the sample, phosphoric acid and air. These materials pass through a single bead string reactor (SBSR) to ensure mixing and are then passed through the modified distillation apparatus (4) of the present invention. Bottoms from the distillation are passed through a heat exchanger (11), cooled and disposed, while the distillate overhead (8) is cooled with a cooling means (15, 16) in a multistage condenser (9) such that a level control (13) stream and a resample stream (10) are obtained. A vent (14) open to atmosphere allows smooth operation of level control stream (13). The bottoms (12) and level control streams (13) are sent through the manifold to waste while the resample (10) is combined with 4-amino-antipyrine in buffer and passed through a single bead string reactor for thorough mixing. Thereafter, the mixed sample is additionally combined with oxidizing agent such as $iron^{+3}$ compound (potassium ferricyanide in buffer) and again passed through a single bead string reactor. This mixture is combined with air, passed through a glass mixing coil to a debubbler (35) and passed to a colorimeter (32) for determination of concentration based on color. Optionally, results are recorded on a chart (33).

The invention is more concretely described with reference to the examples below wherein all parts and percentages are by weight unless otherwise specified. The example is provided to illustrate the instant invention and not to limit it.

EXAMPLE 1

Tests were carried out to determine phenol in water samples across a concentration range of about 5 to about 250 parts per billion. Two milliliter (ml) samples were needed for analysis. In order to determine phenolic concentration, phenolic compounds of the distillate resulting from the apparatus of the present invention were reacted with 4-amino-antipyrine in the presence of potassium ferricyanide in alkaline solution to produce a quinoid type compound (a red dye compound). This red dye compound is monitored by colorimetry at 500 millimeters (mm). The reagents utilized were trisodium, phosphate, boric acid, citric acid, 4-amino-antipyrine, potassium ferricyanide, phosphoric acid, phenol, copper sulfate and deionized water.

A continuous flow system was prepared as described in FIGS. 1 and 2 for use with the distillation phenols. A recycle time of 60 seconds for sampling and 180 seconds for washing was utilized,. A series of 7 descending standards ranging from 250 to 10 parts per billion phenol were used to construct a calibration curve using absorbance values vs standard concentration. Absorbance values of each sample were read and the phenol concentration determined on the curve. The concentration values were multiplied by appropriate dilution factors and reported as parts per billion phenol.

Procedures were used utilizing the apparatus of the present invention as well as a simple distillation coil without an expansion chamber in the heating jacket. Data was collected to show the effect of sample feed rate on the apparent phenol concentration for refinery effluent waters when operating using a prior art distillation coil only in the heating apparatus at 165°. The results are set forth in Table 1.

TABLE 1

| Sample | PHENOL CONCENTRATION (ppb) Flow Rate (ml/min) 165° C. | | |
|---|---|---|---|
| | 1.4 | 2.5 | 3.4 |
| A | 520 | 106 | 140 |
| B | 550 | 120 | 150 |

TABLE 1-continued

| Sample | PHENOL CONCENTRATION (ppb) Flow Rate (ml/min) 165° C. | | |
|---|---|---|---|
| | 1.4 | 2.5 | 3.4 |
| C | 503 | 560 | 110 |

The effect of temperature on the apparent phenol concentration in parts per billion (ppb) for refinery effluent waters when utilizing the prior art distillation coil only in a heating jacket is set forth in Table 2.

TABLE 2

| Sample | PHENOL CONCENTRATION (ppb) Temperature °C. | |
|---|---|---|
| | 173 | 187 |
| A | 270 | 520 |
| B | 240 | 550 |
| C | 260 | 503 |

After installing the apparatus of the present invention, apparent phenol concentration for refinery effluent water samples when operating at various heating bath temperatures and sample feed rates was likewise determined. The much closer determination of phenol concentration using the apparatus of the present invention is shown in Table 3.

TABLE 3

| Feed Rate (ml/min) | PHENOL CONCENTRATION (ppb) Temperature (°C.) | | | |
|---|---|---|---|---|
| | 132 | 150 | 168 | 187 |
| 3.9 | 6800 | 7100 | 7300 | 7500 |
| 2.5 | 7000 | 7100 | 7200 | 7400 |
| 2.0 | — | — | 7300 | 7200 |

Thus it is apparent that the present invention provides a much more reliable method of separating distilland under simple distillation conditions by minimizing the effect of distilland flow rate and heating bath temperature.

While certain embodiments and details have been shown for the purpose of illustrating this invention, it will be apparent to those skilled in this art that various changes and modifications may be made herein without departing from the spirit or scope of the invention.

We claim:

1. A continuous simple distillation apparatus for removal of volatiles from liquid phase comprising
   (a) casing means containing therein a closed conduit for liquid distilland, said conduit surrounded by heating means contained within said casing means;
   (b) a vapor draw means connected directly to said closed distilland conduit, said vapor draw means containing at least one expansion chamber vertically disposed in and surrounded by said heating means, the lower portion of the lowest of said expansion chambers containing inert particulate means to increase surface area, and condenser means connected to said vapor draw means;
   (c) a bottoms draw means disposed in said heating means and connected to the lower portion of the lowest expansion chamber of said vapor draw means, said bottoms draw means exiting substantially vertically from said lowest chamber and being substantially totally filled with said inert particulate means.
2. An apparatus as described in claim 1 wherein the closed conduit is a coil and the inert particulate means is glass beads.
3. An apparatus as described in claim 2 wherein the heating means is a liquid bath.
4. An apparatus as described in claim 3 wherein the liquid bath is capable of operating at a temperature above 200° C.

* * * * *